United States Patent [19]

Petersen et al.

[11] Patent Number: 5,395,377

[45] Date of Patent: Mar. 7, 1995

[54] EXTRAMEDULLARY PROXIMAL TIBIAL GUIDE

[76] Inventors: Thomas D. Petersen, 9680 Alto Dr., La Mesa, Calif. 91941; Dennis W. Burke, 245 Highland St., Milton, Mass. 02186

[21] Appl. No.: 124,505

[22] Filed: Sep. 21, 1993

[51] Int. Cl.⁶ .......................................... A61B 17/56
[52] U.S. Cl. ............................................... 606/88
[58] Field of Search .................... 606/88, 86, 87, 96

[56] References Cited

U.S. PATENT DOCUMENTS

| | | | |
|---|---|---|---|
| 4,841,975 | 6/1989 | Woolson | 606/96 |
| 5,207,680 | 5/1993 | Dietz et al. | 606/86 |

*Primary Examiner*—Tamara L. Graysay
*Attorney, Agent, or Firm*—H. Jay Speigel

[57] ABSTRACT

An extramedullary proximal tibial guide includes a distal end carrying a vertically adjustable ankle bracket as well as an ankle pointer, and a proximal end carrying a saw guide. The saw guide includes a saw guiding slot which is so configured as to have an open area between the bottom of a slot rail and portions of the top of the bone which is to be resected so that the surgeon may precisely view the location of engagement of the surgical saw with the bone structure. The surface area of engagement between the saw guide and the bone is made quite small with a sharp bone contacting edge to facilitate micro adjustment. Laterally of the saw guiding slot, side flares are provided which are designed to protect the patellar tendon and soft tissues during resection. The ankle bracket is held in place about the ankle of the patient through the use of a fastener including a ball chain and a spring. The inventive guide is provided with structures permitting the various required adjustments, which structures are recessed within the guide structure to avoid protrusions which could interfere with the surgical procedure.

20 Claims, 4 Drawing Sheets

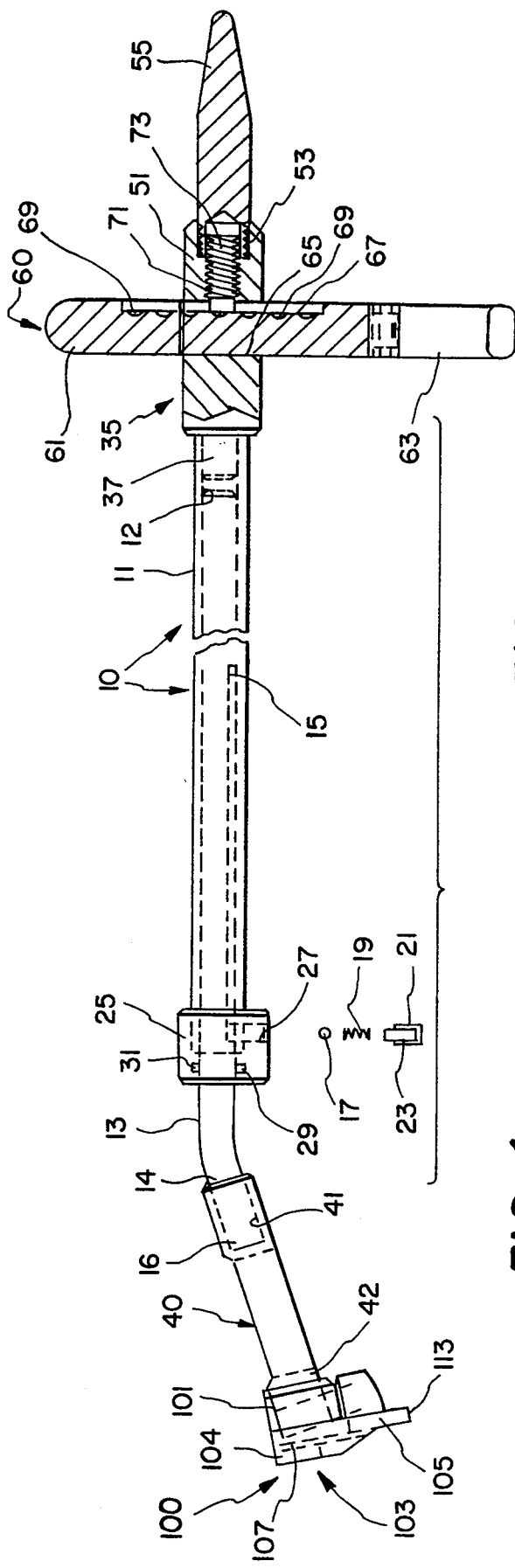
FIG. 2
FIG. 3
FIG. 4

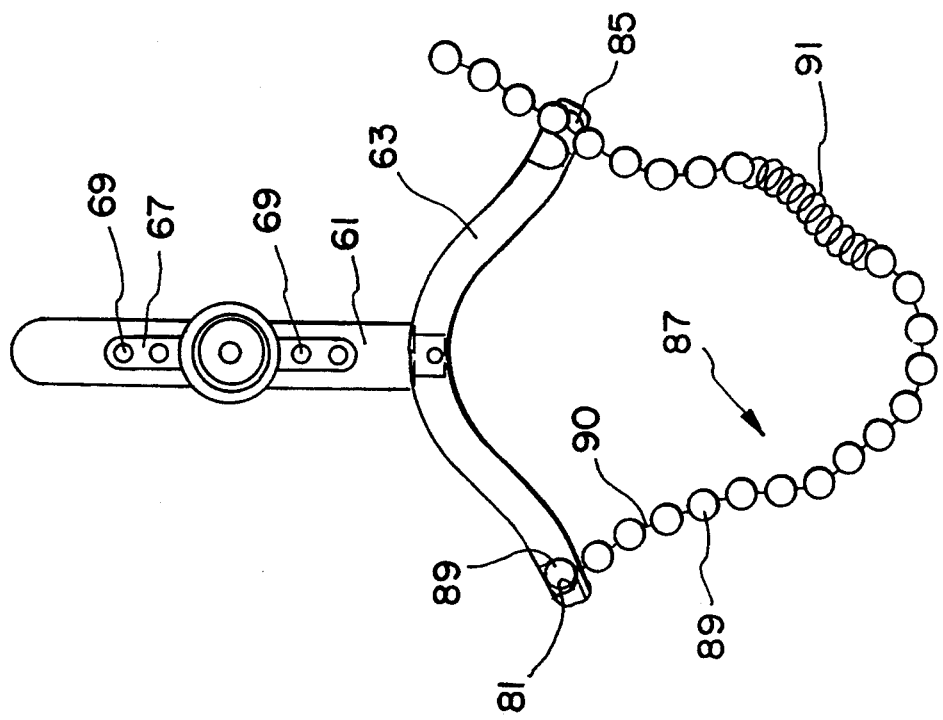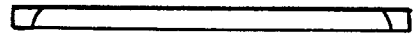

EXTRAMEDULLARY PROXIMAL TIBIAL GUIDE

BACKGROUND OF THE INVENTION

The present invention relates to an extramedullary proximal tibial guide. In the prior art, proximal tibial saw guides are known. However, Applicant is unaware of any such device including all of the features and aspects of the present invention.

Several problems persist in surgical procedures which are employed to install a knee joint prosthesis on a patient. One of the key problem areas concerns resection of the proximal tibia and the present invention is designed to facilitate such resection in a safer, more effective manner.

When resecting the proximal tibia, the patellar tendon must be everted and turned laterally. The attachment of the patellar tendon on the tibial tubercle is quite close to the location where resection is to take place and, as such, it is important to provide an instrument which will protect the patellar tendon during the resection procedure. Applicant is unaware of any prior art tibial saw guide which provides this protection.

In a further aspect, in prior art proximal tibial saw guides, the surface of the guide defining the bottom extent of the saw guide slot traditionally is specifically shaped to mimic the shape of the proximal tibia. As such, with the structure of the saw guide defining the bottom of the slot so that the bottom of the slot on both side walls thereof is flush with the proximal tibial surface, it is not possible for the surgeon to specifically visualize precisely how far from the extreme proximal end of the tibia the resection will take place. As such, a need has developed for a proximal tibial saw guide which may accurately and precisely guide resection of the proximal tibia while permitting the surgeon to visualize the precise location of the resection prior to commencing with the resection.

In a further aspect, while prior art proximal tibial saw guides have included features permitting macro adjustment of the particular position Of the saw guide on the proximal tibia, a need has developed, as surgical techniques have become more precise, to devise a cutting head which may be held in such a manner that micro adjustment is possible. Such micro adjustment requires constraint of the tibial saw guide with fastening means permitting micro adjustments including angulatory adjustments. This problem also arises due to the fact that prior art surgical saw guides for resecting the proximal tibia engage the proximal tibia with a large surface area of engagement. This large surface area of engagement makes it more difficult to perform micro adjustments due to the frictional forces caused by such a large surface area. As such, a need has developed for a surgical saw guide for resection of the proximal tibia which addresses these deficiencies in the prior art.

In prior art proximal tibial saw guides, in order to perform the various adjustments in configuration of the device to permit accommodation to a particular surgical site, large adjustment knobs are often provided. These knobs can sometimes interfere with the surgical procedure and, even where such interference is subtle, a need has developed to provide adjustment means which is more aesthetic than known adjustment means while maintaining full functionality.

In a further aspect, a need has developed for a securing device to secure the ankle bracket to the ankle of the patient which may easily be adjusted while providing secure attachment.

It is with these problems in mind that the present invention was developed.

SUMMARY OF THE INVENTION

The present invention relates to an extramedullary proximal tibial guide. The present invention includes the following interrelated objects, aspects and features:

(A) In a first aspect, the inventive cutting head is specifically designed to protect the patellar tendon during resection. As pointed out above, during resection, the patellar tendon needs to be everted and turned laterally. In order to facilitate this procedure, the inventive cutting head has flared flanges on each side thereof which extend downwardly and laterally in such a way that they reach out underneath the tendon area and protect it from the saw blade during resection.

(B) The saw guiding slot is defined by walls formed in top and bottom rails. In order to permit the surgeon to determine the precise depth of the proximal cut, that is, the distance from the absolute proximal end of the tibia to the specific location of the resection, the top rail is provided with a relieved portion which provides an opening adjacent the bone surface which is to be resected. In this way, the surgeon may insert the saw blade through the slot and may visualize where the saw engages the top of the proximal tibia before commencing the resection.

(C) As pointed out above, a need has developed to provide a proximal tibial saw guide which permits micro adjustment. Where ability to provide micro adjustments is desired, in order to solve this problem, two particular features may be incorporated in the present invention. Firstly, the supporting arm for the saw guide may be provided with a central elongated slot designed to accept a spring-loaded pin. This spring-loaded pin provides the appropriate amount of tension to maintain rigidity of the saw guide while allowing the surgeon to make micro adjustments in the position of the cutting head both longitudinally and angularly. In order to further facilitate such micro adjustments and even where micro adjustments are not carried out, the bottom rail of the saw guide is provided with a sharp edge which engages the proximal tibia to minimize frictional forces therebetween to best facilitate micro adjustments. The inventive instrument may be effectively used in guiding resection of the proximal tibia without such micro adjustments. However, accuracy of resection is enhanced if micro adjustments are possible.

(D) The present invention has been specifically designed to avoid the use of any protruding knobs or other large cumbersome adjustment devices. Thus, vertical adjustment of the ankle bracket is facilitated through the use of a spring biased ball received within a slot having a series of slight part spherical depressions which positively engage the ball at fixed spaced locations therealong. In order to permit firm but easy adjustment of the degree of extension of the expansion rod of the present invention, an O-ring providing frictional interengagement and/or a spring-loaded ball received within a slot are employed to permit easy length adjustment without the use of large tightening knobs. Where the ball and slot are not employed, one may utilize the O-ring in combination with a rotation-preventing pin received within the slot.

(E) To solve the problems which have been present in prior art resection guides concerning firm but easy attachment over the ankle, the inventive ankle bracket has been made of an arcuate shape and a ball chain has been provided having a tension spring incorporated therewith permitting easy adjustment of the tension. The ankle bracket has slots designed to receive the ball chain between any two adjacent balls thereof to permit easy adjustment and fixation.

As such, it is a first object of the present invention to provide an extramedullary proximal tibial guide.

It is a further object of the present invention to provide such an extramedullary proximal tibial guide with means for protecting the patellar tendon during resection.

It is a still further object of the present invention to provide such a tibial guide with view of the bottom rail of the slot to permit the surgeon to view the precise location of resection.

It is a still further object of the present invention to provide structures and features permitting micro adjustment of the longitudinal and angular positioning of the cutting head.

It is a yet further object of the present invention to provide such a tibial saw guide with adjustment means to provide the various adjustments thereof which are hidden from view to provide an extremely smooth and uncumbersome appearance.

It is a yet further object of the present invention to provide such a device with an ankle bracket with easy and effective ankle attachment.

These and other objects, aspects and features of the present invention will be better understood from the following detailed description of the preferred embodiment when read in conjunction with the appended drawing figures.

BRIEF DESCRIPTION OF THE DRAWINGS

FIG. 2 shows a side view, partially in cross-section along the line II—II of FIG. 1, with this figure also being partially exploded.

FIG. 3 shows an exploded side cross-sectional view of a portion of the locking mechanism for the ankle bracket.

FIG. 4 shows an end view of the adjusting screw for the longitudinal length adjustment of the present invention.

FIG. 5 shows an end view of the ankle bracket of the present invention.

FIGS. 6a and 6b show top and end views, respectively, of the top rail of the present invention.

SPECIFIC DESCRIPTION OF THE PREFERRED EMBODIMENT

Figure 1:
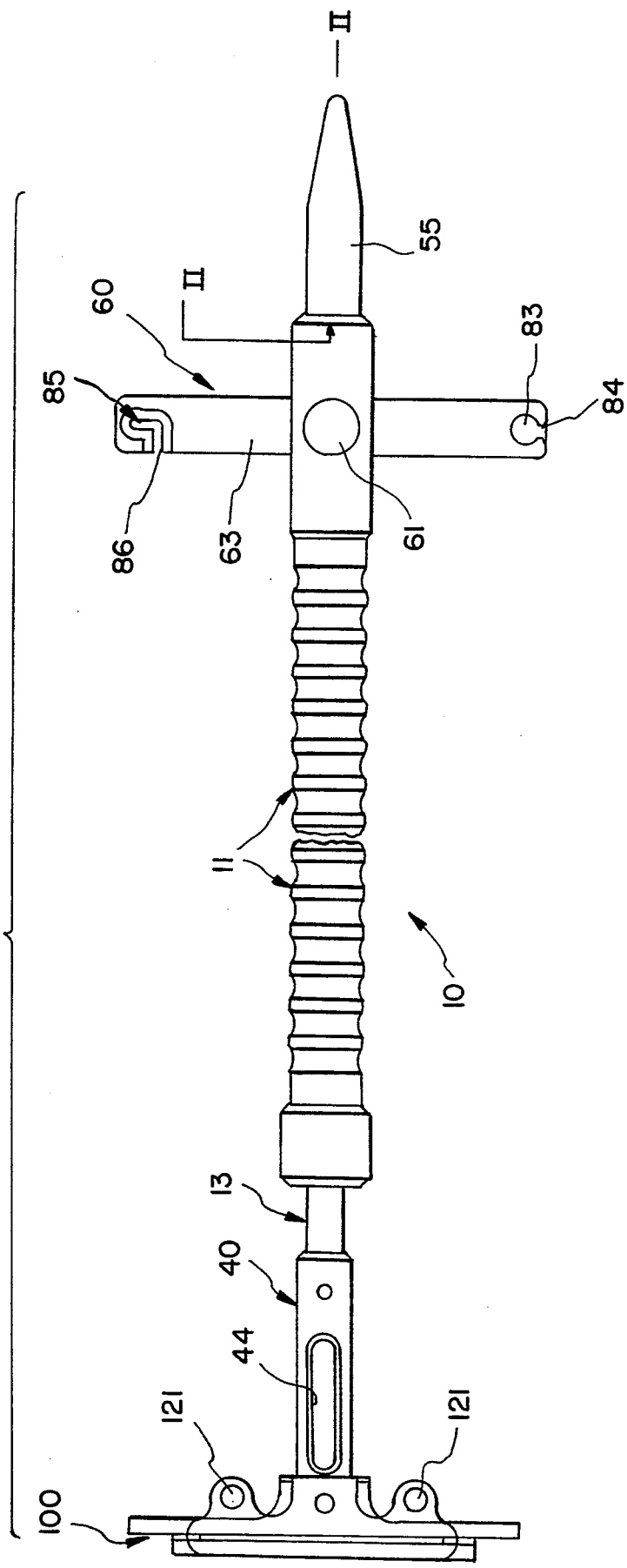
FIG. 1 shows a top view of the present invention.
Figure 8A:
FIGS. 8a and 8b show side and top views, respectively, of the expansion rod of the present invention, showing an elongated slot therein.
Figure 8B:
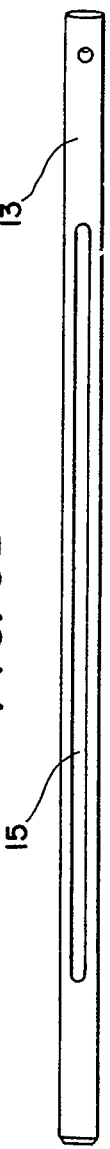

Reference is first made to FIGS. 1 and 2 wherein the present invention is generally designated by the reference numeral 10 and is seen to include a first rod 11 and a second rod 13 which telescopes within the first rod 11. As particularly shown in FIGS. 2, 8a and 8b, the second rod 13 has an elongated slot or longitudinal extending recess 15 designed to receive a ball 17 which is biased by a spring 19 received within the cavity 23 of a spring bias adjustment screw 21 having a threaded periphery and received within a threaded recess 27 of a fitting 25 securely mounted on the proximal end of the first rod 11. As shown in FIG. 4, the screw 21 has a slotted recess 22 designed to receive a tool having a correspondingly shaped tool end to permit rotation of the screw 21 and thereby adjustment of the spring force of the spring 19.

As also shown in FIG. 2, the fitting 25 includes a recess 29 which receives an O-ring 31 comprising frictionally operative locking mean designed to frictionally engage the outer surface of the second rod 13. The frictional forces imposed on the second rod 13 by the ball 17 and/or the O-ring 31 allow the surgeon to adjust the degree of extension of the rod 13 with respect to the rod 11 while facilitating firm retention of the particular chosen position due to the frictional forces imposed by the ball 17 and/or the O-ring 31. As shown in phantom in FIG. 2, the first rod 11 has an internal passageway 12 extending throughout its length to permit the telescopic adjustment of the position of the second rod 13 with respect thereto. At the end of the first rod 11 distal from the fitting 25, an ankle bracket support 35 is provided which has a projection 37 which is received within the passageway 12 of the first rod 11, to firmly attach the ankle bracket support thereto. As also shown in FIG. 2, in particular, the end 14 of the second rod 13 is bent and includes an end 16 received within a recess 41 of the slot support 40. The position of the ball 17 within the slot 15 comprises alignment means which facilitates maintenance of the appropriate rotational alignment between the second rod 13 and the first rod 11.

With particular reference, now, to FIGS. 1, 2 and 5, the details of the ankle bracket will now be described. As shown, the first end 51 of the ankle bracket support 35 includes a threaded recess 53 in which is threadably received the threaded end of an ankle pointer 55 specifically designed to permit the surgeon to locate the mechanical axis of the leg and attach the inventive device 10 in alignment therewith. The ankle bracket is generally designated by the reference numeral 60 and is seen to include a vertical attachment member 61 and an arcuate ankle engaging portion 63 extending laterally to either side of the attachment member 61. The attachment member 61 is slidably received within a passageway 65 formed through the ankle bracket support 35.

As particularly shown in FIGS. 2 and 5, the attachment member 61 has a recess 67 with a series of vertically spaced part spherical depressions 69 formed therein. Within the recess 53 of the support 35, a threaded counter bore 71 is provided which receives a threaded screw 73, also shown in FIG. 3, and which includes an internal bore 75, shown in phantom in FIG. 3, designed to receive a compression spring 77 designed to bear against the ball 79, which structures are shown in exploded representation in FIG. 3. The ball 79 is designed to engage in one of the part spherical depressions 69 as the attachment member 61 is moved with respect to the passageway 65 to provide firm fixation of the vertical location of the ankle bracket 60 in one of the seven discrete positions provided by the part spherical depressions 69. As shown in phantom in FIG. 3, the end of the screw 73 remote from the bore 75 may be provided with a tool receiving recess 81 similar to the tool receiving recess 22 of the screw 21 to allow adjustment of the degree of spring force imparted to the ball 79 by the spring 77. Access to the tool receiving recess 81 of the screw 73 may easily be obtained through removal of the ankle pointer 55 from the threaded recess 53.

In a further aspect, with particular reference to FIGS. 1 and 5, it is seen that the bracket 63 has a first slot 83 and a second L-shaped slot 85 at the extreme ends thereof. As shown in FIG. 5, fastening means comprising a ball chain 87 having a series of balls 89 as well as an intermediate tension spring 91 is provided to allow firm attachment of the ankle bracket 60 over the ankle of the patient. Thus, one of the balls 89 may be inserted within the recess 83 through the provision of the opening 84 in the slot 83 which permits the wire 90 interconnecting adjacent balls 89 to pass therethrough whereupon one of the balls 89 may seat in the recess 83 as particularly shown in FIG. 5. In a similar way, the opening 86 in the slot 85 permits the surgeon to fix one of the balls 89 in the slot 85 as particularly shown in FIG. 5. In practice, the surgeon will choose which ball 89 is to be inserted within the slot 85 by pulling the chain 87 tight enough so that there is at least slight tension on the spring 91 to provide a resilient restoration force tending to firmly fix the chain 87 and thereby the bracket 60 in position over the ankle of the patient.

Figure 9:
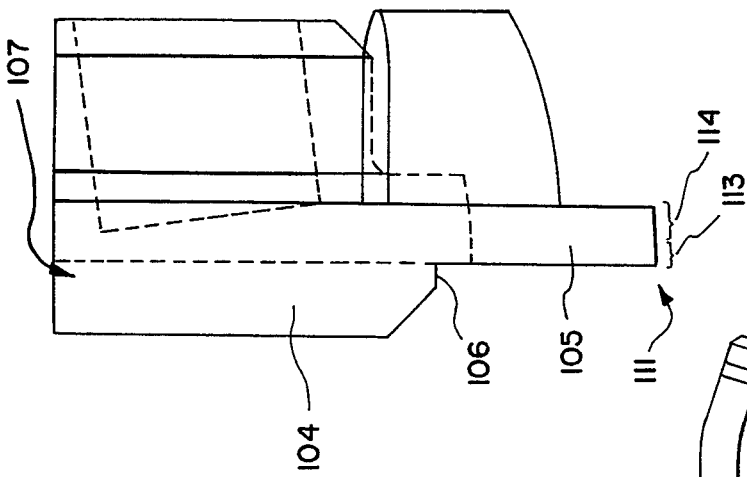
FIG. 9 shows an enlarged view of the cutting head of the present invention.

Particular reference is now made to FIGS. 1, 2, 6a, 6b and 7 for a description of the inventive cutting head of the present invention. The cutting head is generally designated by the reference numeral 100 and includes a first opening 101 (FIGS. 2 and 7) designed to receive the second end 42 of the slot support 40 to fix the cutting head 100 thereto. The cutting head 100 has a second end 103 defined by a top rail 104 which, with the adjacent bottom rail 105 having facing surfaces which define therebetween the saw guiding slot 107. With reference to FIGS. 7a and 7b, the position of the top rail 104 on the bottom rail 105 is shown by the bottom edge 106 of the top rail 104. As particularly shown in FIG. 7b, the bottom rail 105 includes lateral flared flanges 109 which are specifically designed to reach out underneath the tendon area to protect the patellar tendon from the saw blade during resection. The bottom rail 105 also includes an extremely thin bottom bone engaging surface 111 which is arcuate in the medial-lateral direction, as shown, and is designed with a first portion 113 which is flat in the anterior-posterior direction and sits on the top of the proximal tibia with an extremely narrow area of interengagement as is best understood from viewing FIG. 9. A second portion 114 of the surface 111 is arcuate both in the anterior-posterior direction and in the medial-lateral direction. As should be understood from FIGS. 7a and 7, the area of the saw guiding slot 107 between the bottom edge 106 of the top rail 104 and the bottom edge 111 of the bottom rail 105 is completely open allowing the surgeon to view the precise location where the resection is to take place. In practice, the surface ill sits on the anterior edge of the proximal tibia and defines the distal edge of the resection. Thus, the surgeon may easily see the precise location of resection since the top rail 104 is quite relieved as compared to the bottom rail 105, as particularly shown in FIG. 7b.

In the preferred embodiment of the present invention, the surface 114 is arcuate in the anterior-posterior direction so that the surface of engagement between the surface 113 and the proximal tibia is as small as possible, approaching line contact. In this way, adjustments of the particular position and orientation of the cutting head 100 with respect to the proximal tibia may be easily accomplished with minimal frictional deterrence.

The inventive cutting head 100 includes features in conjunction with other features of the inventive device 10 which best facilitate fixation in the precise position desired for effective resection of the proximal tibia. Thus, the cutting head 100 includes fixation pin receiving openings 121. Furthermore, the slot support 40 includes an elongated slot 44 which is designed to receive a spring-loaded pin. The use of a spring-loaded pin in this particular environment allows quite effective micro adjustment of the position of the cutting head laterally and angularly. The spring-loaded pin provides just the right amount of tension, in this environment, to maintain rigidity while allowing the surgeon to micro adjust the position of the cutting head. Of course, as explained above, micro adjustment using the spring-loaded pin is an optional feature. However, micro adjustment is feasible using a standard pin provided the standard pin is not attached too tightly.

Figure 7A:
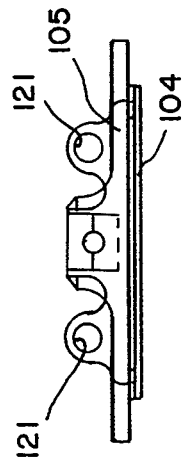
FIGS. 7a and 7b show top and end views, respectively of the bottom rail of the present invention with the top rail superimposed thereover.
Figure 7B:
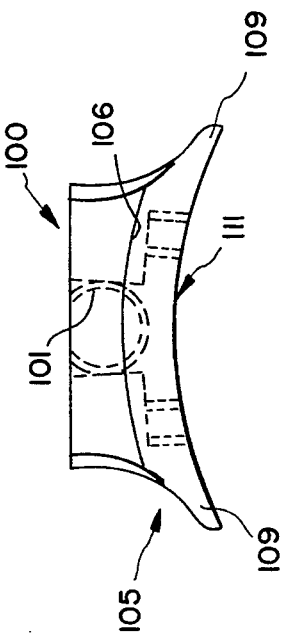

With the inventive device 10 having been described in great detail, its preferred mode of use will now be described. Firstly, the ankle bracket 60 is mounted over the ankle of the patient and the ball chain 87 is adjusted as shown in FIG. 5 to provide slight tension on the spring 91 to provide firm fixation. The second rod 13 is adjusted with respect to the first rod 11 by overcoming the frictional forces of the ball 17 in the slot 15 and/or those imposed on the periphery of the second rod 13 by the O-ring 31 so that the second rod 13 may be extended to an appropriate length permitting location of the surface 113 of the cutting head 100 in the appropriate location. Through adjustment of the position of the ankle bracket support 35 with respect to the attachment member 61, through interengagement with the ball 79 within one of the part spherical depressions 69, the angulation of the cutting head 100 in the anterior-posterior direction may be fine tuned. In such position, due to the relationship between the top rail 104 and the bottom rail 105, as best seen in FIG. 7b, the surgeon may extend the surgical saw blade through the slot 107 to view where the location of the resection would be in this particular configuration of the device 10. With the saw blade so projected through the slot 107, the position of the second rod 13 with respect to the first rod 11 as well as the position of the attachment member 61 with respect to the ankle bracket support 35 may be further adjusted to further adjust the precise position of the surface 113 on the proximal tibia.

Additionally, the flared sides 109 of the bottom rail 105 may be positioned underneath the tendon area to isolate the tendon area from the cutting slot 107 and thereby protect the patellar tendon and soft tissues from damage during resection.

Fixation of the cutting head may be accomplished through insertion of a spring-loaded pin through the slot 44 in the slot support 40. With the pin so inserted, further micro adjustments may be accomplished until the precise positioning of the cutting head 100 has been accomplished. Thereafter, further pins may be inserted through the pin receiving openings 121 of the cutting head 100 to provide final fixation.

Thereafter, resection may be accomplished while the surgeon may view the location of resection as should best be understood from FIGS. 2 and 7b.

After resection has occurred, the inventive device 100 may be suitably removed from the patient's leg through removal of the pins from the pin receiving openings 121, removal of the spring-loaded pin from the slot 44 and unfastening of the chain 87 from the ankle bracket 60.

As such, an invention has been disclosed in terms of a preferred embodiment thereof as well as the method of using the said embodiment in performance of orthopedic surgery, which invention fulfills each and every one of the objects of the invention as set forth hereinabove and provides a new and useful extramedullary proximal tibial guide of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

We claim:

1. A proximal tibial resection guide, comprising:
   a) an elongated rod having a proximal end and a distal end, said rod having an adjustable length;
   b) an ankle bracket attached to said distal end of said rod, said ankle bracket including fastening means for releasably fastening said ankle bracket to an ankle of a patient; and
   c) a cutting head attached to said proximal end of said rod, said cutting head including a top rail and a bottom rail, said cutting head having a saw guiding slot defined between said rails, said bottom rail having a bone engaging surface, said top rail terminating spaced above said bone engaging surface leaving a portion of said bottom rail adjacent said bone engaging surface exposed to view, said top rail being proximal of said bottom rail whereby a surgeon may insert a saw through said slot and may view a precise position of said saw over a proximal tibia of a patient prior to resection so that precise positioning of said cutting head may be accomplished.

2. The guide of claim 1, wherein said elongated rod comprises a first rod and a second rod telescopingly received within a passageway formed in said first rod, and frictionally operative locking means between said rods for holding said rods in a fixed adjusted degree of extension with respect to one another.

3. The guide of claim 2, wherein said locking means comprises an O-ring surrounding and engaging said second rod and through which said second rod reciprocates.

4. The guide of claim 3, wherein said locking means further includes alignment means for maintaining rotative alignment between said first and second rods.

5. The guide of claim 4, wherein said alignment means comprises a fitting attached to said first rod and carrying a biased projection, and a longitudinally extending recess in said second rod receiving said projection.

6. The guide of claim 5, wherein said biased projection comprises a spring biased ball.

7. The guide of claim 1, wherein said cutting head includes at least one flange extending laterally of said slot and located laterally of said bone engaging surface, said at least one flange being adapted to engage a patellar tendon and protect said tendon from a saw extending through said slot.

8. The guide of claim 7, wherein said at least one flange comprises two laterally extending, oppositely directed flanges.

9. The guide of claim 1, wherein said fastening means comprises an elongated chain.

10. The guide of claim 9, wherein said chain comprises a ball chain, and further including a tension spring incorporated in said chain.

11. The guide of claim 10, wherein said ankle bracket includes an arcuate bracelet member having opposite ends each of which includes a chain attaching slot.

12. The guide of claim 1, wherein said ankle bracket is attached to said distal end of said rod via an adjustable connection.

13. The guide of claim 12, wherein said adjustable connection comprises a post on said ankle bracket received through a passageway through said distal end of said elongated rod.

14. The guide of claim 1, wherein said bone engaging surface is thin whereby said cutting head is engageable with a proximal tibia with a small area of contact.

15. The guide of claim 14, wherein said bone engaging surface is arcuately curved in a medial-lateral direction as well as in an anterior-posterior direction.

16. A proximal tibial resection guide, comprising:
   a) an elongated rod having a proximal end and a distal end, said rod having an adjustable length;
   b) an ankle bracket attached to said distal end of said rod, said ankle bracket including fastening means for releasably fastening said ankle bracket to an ankle of a patient; and
   c) a cutting head attached to said proximal end of said elongated rod, said cutting head having a top surface and a bottom surface and a saw guiding slot extending therebetween, said bottom surface being extremely thin and being arcuately curved in a medial-lateral direction as well as in an anterior-posterior direction whereby said cutting head engages a proximal tibia with an area of contact approaching line contact.

17. The guide of claim 16, wherein said cutting head is attached to said rod via a slot support having a pin receiving slot therethrough.

18. The guide of claim 17, wherein said cutting head further includes at least one fixation pin receiving opening.

19. A proximal tibial resection guide, comprising:
   a) an elongated rod having a proximal end and a distal end;
   b) a cutting head attached to said proximal end and having a saw guiding slot extending therethrough;
   c) an ankle bracket attached to said distal end via a vertically adjustable connection, said ankle bracket having an arcuate bracket member and a chain releasably attachable to said bracket member so that said bracket member may be releasably fastened to a patient's ankle.

20. The guide of claim 19, wherein said chain comprises a ball chain carrying a tension spring.

* * * * *